United States Patent [19]
Cosman

[11] Patent Number: 5,947,981
[45] Date of Patent: *Sep. 7, 1999

[54] HEAD AND NECK LOCALIZER

[76] Inventor: Eric R. Cosman, 872 Concord Ave., Belmont, Mass. 02178

[ * ] Notice: This patent issued on a continued prosecution application filed under 37 CFR 1.53(d), and is subject to the twenty year patent term provisions of 35 U.S.C. 154(a)(2).

[21] Appl. No.: 08/795,241

[22] Filed: Feb. 19, 1997

Related U.S. Application Data

[63] Continuation of application No. 08/382,226, Jan. 31, 1995, abandoned.

[51] Int. Cl.[6] .................................................. A61B 19/00
[52] U.S. Cl. .......................................... 606/130; 128/869
[58] Field of Search ........................... 606/130; 128/869, 128/870, 858, 559

[56] References Cited

U.S. PATENT DOCUMENTS

| | | | |
|---|---|---|---|
| 4,454,870 | 6/1984 | Schwentker | 128/75 |
| 4,608,977 | 9/1986 | Brown | 606/130 |
| 4,618,978 | 10/1986 | Cosman | 606/130 |
| 4,841,965 | 6/1989 | Jacobs | 606/130 |
| 4,979,519 | 12/1990 | Chavarria et al. | 128/857 |
| 5,040,547 | 8/1991 | Bergstrom | 128/858 |
| 5,263,494 | 11/1993 | Margelos et al. | 606/130 |
| 5,464,411 | 11/1995 | Schulte et al. | 606/130 |

*Primary Examiner*—Michael Buiz
*Assistant Examiner*—Kevin Truong
*Attorney, Agent, or Firm*—Richard J. Birch; Darby & Darby

[57] ABSTRACT

A head and neck positioner and immobilizer having an over-arm structure that can be reproducibly attached to a couch, either CT or MR imaging couch or a treatment couch as for a LINAC radiosurgery system. The positioner enables adjustable immobilization of the patient's head. The over-arm accepts a graphic reference with fiducials such as points, rods, or diagonals that can reference a selected target position determined from tomographic imaging, such as CT or MRI slices or imaging data, to the over-arm or to the couch onto which the arm is attached. Alternately, a target localizer or positioning device can be attached to the over-arm or to the couch to which the arm is attached for positioning the coordinates of the selected target position as determined using the image scan data with the graphic reference fiducials observed in it. The target localizer enables referencing of external apparatus, such as the collimator for X-ray radiation from a LINAC, to be directed to the physical position of the selected target position with reference to the LINAC couch.

17 Claims, 7 Drawing Sheets

HEAD AND NECK LOCALIZER

This application is a continuation of application Ser. No. 08/382,226 filed on Jan. 31, 1995 now abandoned.

BACKGROUND TO THE INVENTION

Heretofore a typical patient stereotactic apparatus has involved a head ring which is attached by posts and sharpened head screws to the patient's cranium, as shown in FIG. 1. The ring 11 encircles the patient's head 12, and is secured to the head by posts such as 14 with head screws 15 at the tips of the posts that can be securely placed into the outer table of the patient's skull. Alternately, the ring may have a dental impression means to register to the patient's teeth (see Radionics GTC System), or the ring may have a mask mold of the face or head to immobilize relative to the head external contours (see the Fisher Heidelberg Mask System). The ring can accept graphic reference localizers which enable scanner index data from tomographic scanning such as CT, MR, P.E.T., etc. to be used to relate two-dimensional or three-dimensional tomographic scan data from an image scanner to the coordinate reference frame of the ring 11. Once the "stereotactic coordinates" of a selected target position seen in the image scan data are determined relative to ring 11, a stereotactic arc system can be used attached to the ring to direct a probe to the physical target corresponding to the selected target position seen from these scan image data. In another context, the ring can be attached to a couch such as 18 by means of ring holders 16, and a delivery of radiation from a LINAC through a collimator system such as 17 can be directed to the stereotactic target coordinates of the selected target position. These are examples of stereotaxy using a patient immobilizer and graphic reference means from the prior art, and are illustrated by the apparatus such as the BRW Stereotactic System of Radionics, Inc.

The use of skull-attached head rings or dental impression or mask impression-attached head rings has limited usefulness for irradiation of the head region. Specifically, the ring is an obstruction to probe and also to radiation beams, for which it may be desirable to aim at targets at the very lowest part of the skull, the nasal pharynx, jaw, neck, and upper thorax. In this situation, a ring structure placed around the head, as shown in FIG. 1, is obstructive and an impediment to desired beam entry directions. The ring can be placed high on the patient's head, but this too may limit the solid angle of access of the beams to the skull base and nasopharynx. The head ring also may prevent wide angulation of the head relative to the couch in some cases.

The patent of Abele and Koslow, U.K. Patent 2,094,590 shows a mouth bite piece type head stabilizer with upright structures, but it has no use of graphic reference means and/or target localizers, it has no biasing means that can effectively stabilize the head movements, it has no repeat positioning to different couches, it is not minimally obstruction-free, it does not use cooperative dental impression, plus biasing means, plus occipital impression means to fix a head or neck position (dental may be substituted here by external contour fixation as shown below), and there are further limitations to the U.K. 2,094, 590 invention which the present invention solves.

It is therefore an object of the present invention to provide a head and neck immobilizer, graphic reference means, and/or target localizer that can reposition the patient's head and neck on a couch, and thereafter provide target localization for probe or external irradiation to targets in the head and neck region.

It is further an objective of the present invention to provide a patient immobilizer which is minimally invasive or non-invasive, thus making it convenient and comfortable for a patient who must be placed on a radiation couch repeatedly for fractionated radiation treatments.

Another objective of the present invention is to provide a nearly obstruction-free immobilization device with nonetheless verniated position and angle capability so the patient's head can be oriented conveniently on, for example, a radiation couch and on an imaging couch.

Another objective of the present invention is to provide a patient immobilizer which yields minimal obstruction to radiation beams in solid angles coming from below the skull base or approaching the nasopharynx and neck.

It is an objective of the present invention to give reliable and accurate target localization and head positioning in the mobile region of the nasopharynx and neck for reproducible and precise target positioning and beam delivery in this critical area, especially near the spine and critical organs of the throat to enable high dose delivery to cancerous tumors and minimal dose delivery to critical or radio-sensitive structures nearby.

It is further an objective of the present invention to provide a target localizer and/or graphic reference means which are registered in the same way to the head and nasopharynx so that perturbations of external apparatus, couch, and body movement will minimally affect accurate target localization. The apparatus of the present invention can be used for stereotactic radiosurgery and stereotactic radiotherapy in these regions. It is amenable to use with computer software, computer workstation-based three-dimensional radiation planning, and for target volume and beam delivery. Embodiments of minimally invasive examples of the present invention using registration to the teeth and to the body extremities and/or external contours will be given, and illustration of various biasing means relative to the patient attachment means (dental or contour based) and relative to the over-arm or couch are given.

DESCRIPTION OF THE INVENTION

Figure 1:
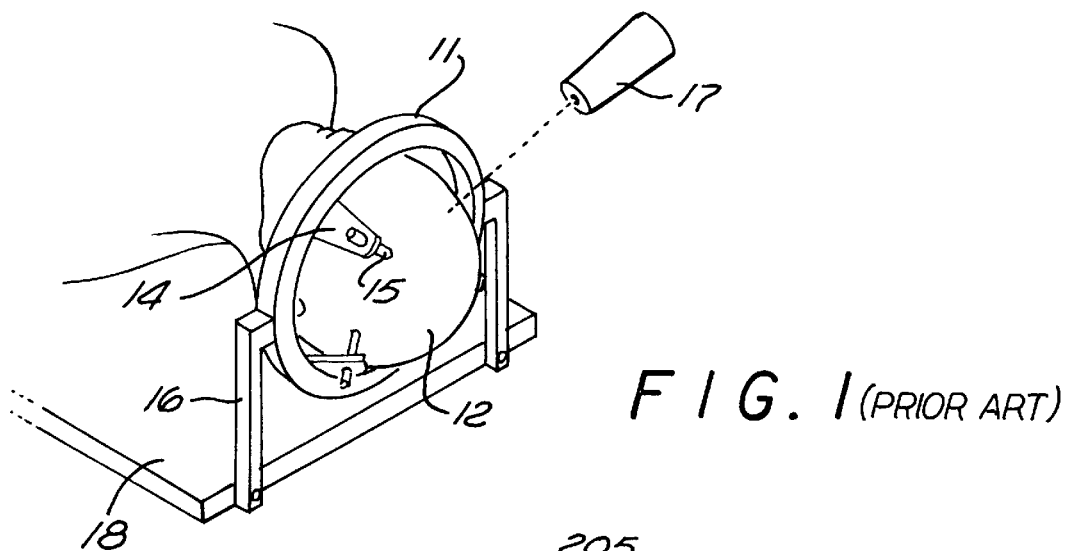
FIG. 1 shows the prior art of head ring based stereotaxy.
Figure 2:
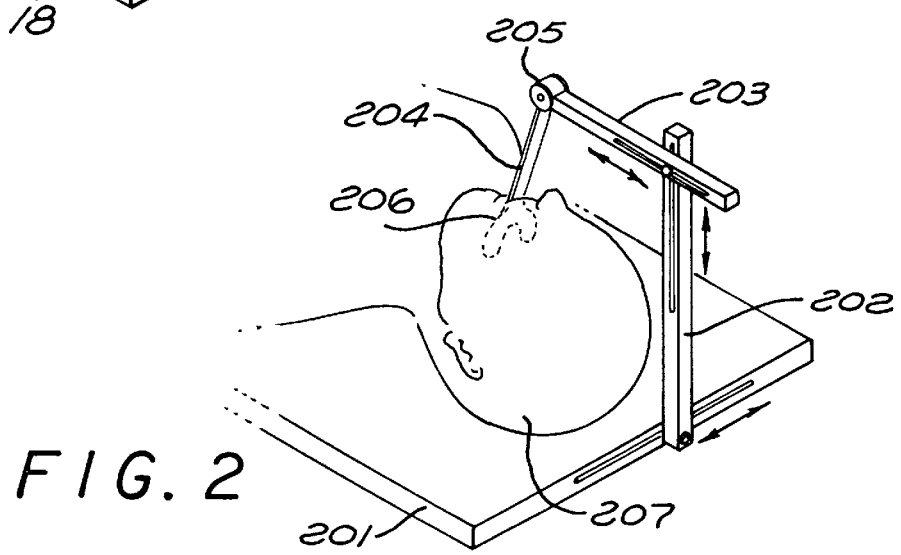
FIG. 2 shows an example of an over-arm patient immobilizer of the present invention.

Referring to FIG. 2, the couch 201 could be the couch of an imaging scanner such as a CT or MR machine, the couch of a simulator, a couch of a radiation therapy machine such as a linear accelerator (LINAC), or any other couch of imaging or stereotactic therapy device. The embodiment shown in FIG. 2, which is an example of the present invention, includes an arm structure which has, in this case, a vertical element 202, a horizontal element 203, a last link 204, which articulates on joint 205, and there is a dental impression tray 206 which is fit to the patient's mouth or teeth. This embodiment illustrates how the arm structure, or over-arm, is in substantially a para-sagittal orientation, that is, mounts on the couch and comes over the patient's head from the top. This can be of advantage because it leaves open the sides and lower hemisphere approaches to the skull base, head, and neck for radiation or other stereotactic approaches. The patient 207 may rest on the couch 201, and the posterior or occipital portion of his head can either lie flat on a couch or can be supported by a curved or molded occipital impression or headrest to further stabilize it, and this occipital headrest may be on the couch itself or attached to the over-arm or in some other way to the apparatus. The essentially horizontal element 203 can be moved horizontally or vertically relative to element 202, as shown by the arrows, and thus the position of the joint 205 over the patient's mouth can be adjusted according to the size of the patient's head and its orientation on the couch. The joint 205 provides a rotation joint which can change the angulation of the last link 204 so as to fit into the patient's mouth with the patient's head orientation as desired by the image scanning or the radiation or stereotactic therapy apparatus or approach. The articulation of the over-arm structure 202, 203, 205, 204, and the patient attachment, in this case dental tray 206, can have many variations, and the joints can be articulated joints, sliding joints, and the arm can have a variety of shapes.

Figure 3:
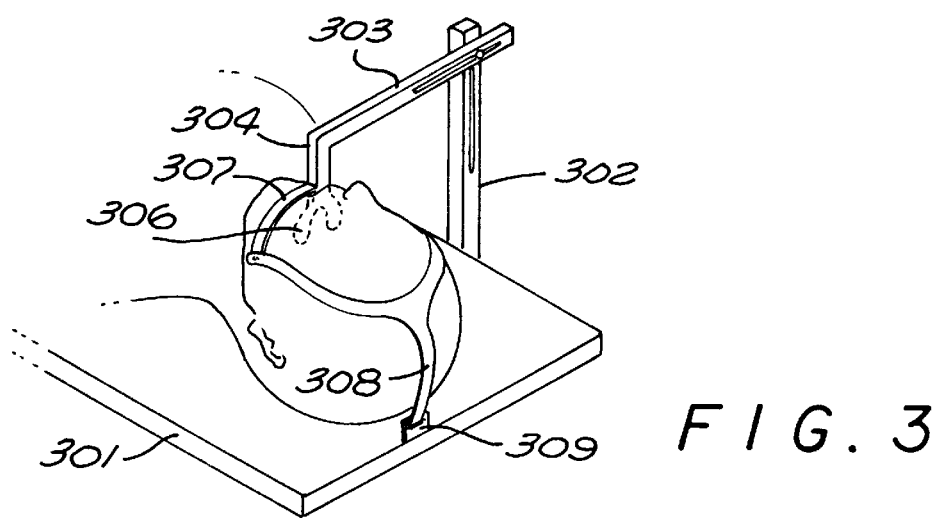
FIG. 3 shows a lateral or side-positioned over-arm according to the present invention.

Referring to FIG. 3, another variation of the over-arm patient immobilization device is shown in which the vertical element 302 is located laterally to the patient's head, and a horizontal element 303 goes back over toward the mid-line of the patient with last link 304 going down to provide the dental tray 306 into the patient's mouth. Lateral structures 307 emerge from both sides of the patient's mouth in this case to support a biasing strap 308, which secures the dental tray firmly to the upper dentition of the patient's mouth and also to the clasp 309 which is secured to the couch 301. This dental impression and biasing strap means is analogous to the usage for the relocatable head ring-based device, referred to as the GTC, made and sold by Radionics, Inc. In the present situation, no ring is use, but the illustrations show an over-arm structure(s) with their adjustment in position relative to the couch, as described and claimed as part of this invention. The examples in FIGS. 2 and 3 show how the space around the patient's head can be made nearly obstruction-free from all directions. Minimal obtrusion to radiation beams and/or X-ray imaging beams is possible with these embodiments, making it possible to irradiate the skull base, nasopharynx, and neck without need to compensate for much intervening material associated with the patient immobilizer.

It is noted in this example that the biasing means, in this case a strap, is connected directly to the dental tray (this could also be a skin contour, etc.), and the bias force is not supplied through the over-arm structure itself. This can be very important in some cases, since it means the patient stabilization is somewhat decoupled from the arm means, the latter being dedicated substantially to positioning in angle and translation. FIG. 3 embodiment illustrates that embodiment of a biasing means that is substantially independent, or decoupled from, or not directly mediated through the over-arm or upright means. That kind of subset of the overall invention is also claimed herein as a specific example of the more general present invention.

Figure 4:
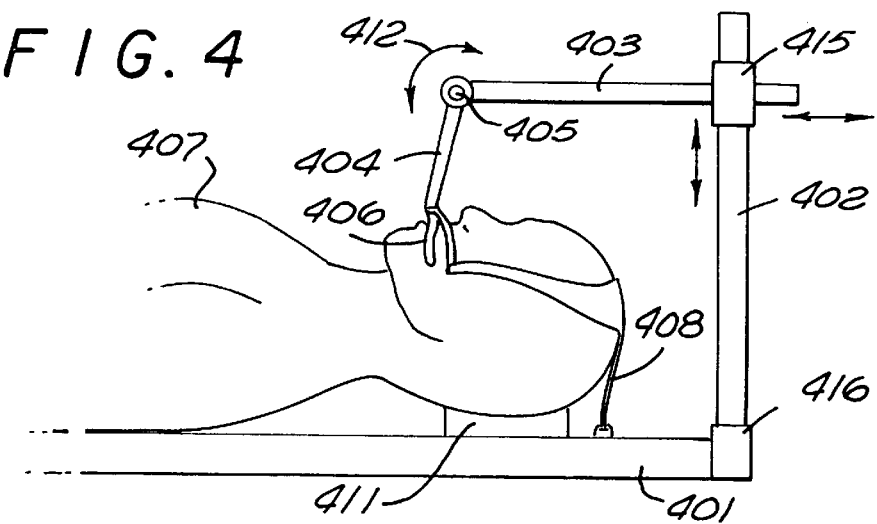
FIG. 4 shows a side view of the over-arm immobilizing the patient by dental impression, occipital impression mold, and biasing straps.

FIG. 4 shows a side elevation view of the patient 407 resting on couch 401 and, in this case, with a molded occipital cast 411, which can be molded to the exact shape of the patient's head or can be a generic, concave cushion made of rubber, foam, bean-bag material, etc. The joint 405 rotates in the direction indicated by the arrow 412 so as to have an adjustable aspect of the last link 404 into the patient's mouth. In this case, a dental impression 406 is being used, and biasing strap 408 is also in place, securing the dental tray solidly to the upper dentition and forcing his head down onto the cushion 411. This strap could have a number of configurations, but the bilateral, frontal straps, together with a posterior pull is convenient. Other biasing devices could be devised that are not straps, such as pull rods, turn buckles, screw take-ups, etc. The slider joint 415 provides dual translations (see the arrows) of the horizontal element 403 relative to the vertical element 402 for adjustment effectively of the longitudinal position and of the height of the dental tray relative to the patient's head. A horizontal movement in and out of the page might also be possible for this over-arm structure relative to the couch, not shown. By this means the position, translation, and orientation of the patient's head can be fully adjusted by the over-arm, the joints and rotations locked up, and the patient thus immobilized for the image scanning or radiation or other stereotactic implementation. This can be done repeatedly, since the entire arm can be locked in place, preserved as such, and brought back and refitted to the couch by a joint means schematically indicated by 416. This, for example, could be a couch clamp that could be fit to a CT scanning couch and later to a treatment radiation therapy couch, and back onto the scanner, and/or back onto the radiation couch for repeated relocations in the same orientation of the patient.

Figure 5:
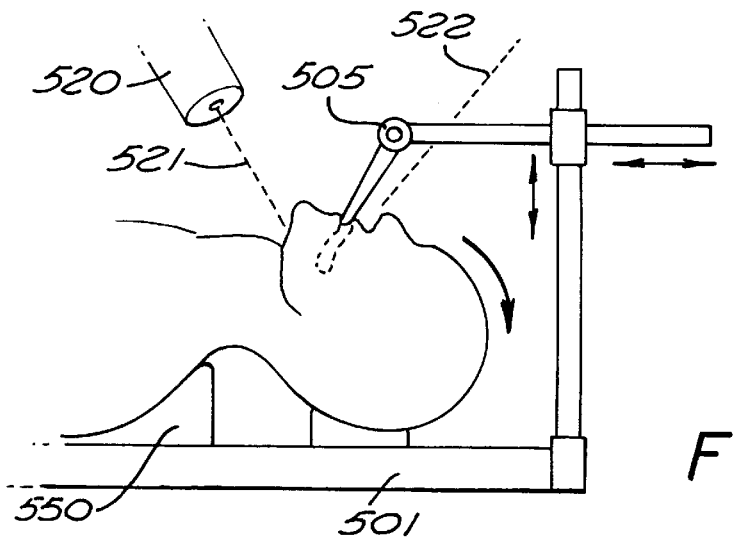
FIG. 5 shows the articulation capability of the embodiment of FIG. 4.

Referring to FIG. 5, one sees the device of FIG. 4, but in this case the joint 505 is in a significantly different angular orientation relative to the rest of the over-arm assembly and relative to the couch 501, so that the patients head is rotated back in the direction shown by the arrow. This is convenient when a beam of radiation needs to be delivered from below, as indicated by the collimator 520, which might deliver an X-ray beam 521 indicated by the dotted line. This X-ray beam would be coming into the throat region or the neck. One sees that the localizer gives no obstruction to the lower portions of the cranium and the neck by this over-arm device. Most of the beam directions, also indicated by the dashed line 522, are unobstructed, with the exception of the beam which passes through the relatively narrow cross-sectional area of the over-arm. Thus, this kind of design provides an obstruction-free patient immobilization means with great flexibility in orientation of the patient, depending on the imaging, or the radiation, or other stereotactic treatment needs. Also shown here is a molded or contour cushion 550 which could be used to stabilize the patient's shoulders relative to the neck and/or head which can improve target positioning, especially in the neck or thorax.

Figure 6:
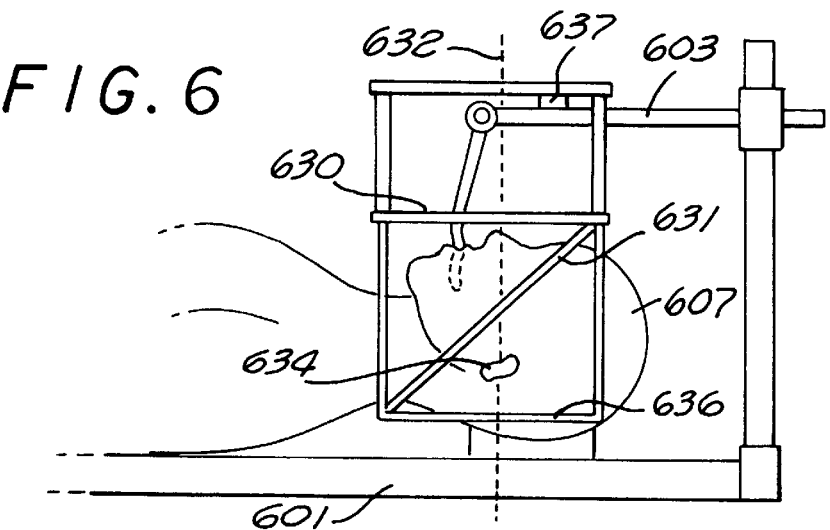
FIG. 6 shows the use of a diagonal and/or rod-based graphic localizer frame with the over-arm.

Referring to FIG. 6, a second element of the present invention is indicated, and this is referred to as the graphic reference means. The over-arm structure is as shown in FIGS. 4 and 5, but in this case the horizontal arm 603 has attached to it the graphic reference means which comprises, in this particular example, horizontal bars 630 and a diagonal element 631 which provides graphic reference indicia for image scanning if the patient were on a tomographic couch, for example, indicated by couch 601. A scan slice such as 632, indicated by the dotted line (this is actually a two-dimensional slice perpendicular to the page). It would intersect the patient's anatomy 607 to give a set of two-dimensional scan image data which includes, in this situation, a target 634, which might be a tumor. Also in that slice would be the intersection with the graphic reference means structures 630, 631, and 636. Again, in this situation, a dental tray is the means of patient contact. The graphic reference means is secured to arm element 603 by the securing element 637.

The example of the graphic reference means in FIG. 6 is only one of many possible embodiments. The graphic reference means could have N-shaped structures with vertical and diagonal rods, as in the case of FIG. 6, where the angle between the structures can be highly variable. The diagonals can be at 45°, in which case the measurement of distances becomes very simple, without need for computed calculations. Since the slope of the diagonal relative to vertical rods is unity, the index identification is accordingly very simple in terms of mapping of distances between index spots from the rods and diagonals and vertical level or slice position of the two-dimensional image slice data. The index data from such a graphic reference means enables a referencing of the scan image data and patient's anatomy relative to the mechanical structures of the over-arm and/or to the couch. In this way, the anatomical data of the patient can be referenced to external apparatus. The aiming of a probe or external beam can be quantitatively made relative to the over-arm, and therefore to the patient's body. This may be done by the target localizer to be described below. The graphic reference means may have widely varying configurations and types of index structures. For example, the indicia could be radiopaque index spots that are seen on some slices, but perhaps not all. The rod structures as shown in FIG. 6 may be in the form of V-shapes, or they can be wedge-shaped plates or other mechanical variations which give variable data on the scan image data so as to produce the mapping, transformation, or referencing of the data seen on the image scanner to the external apparatus that is connected to the patient's body. The index dots can be MRI compatible, CT compatible, P.E.T. compatible, etc. so they can be compared in different imaging modalities. Once the registration of the scan image data of the patient's anatomy and the selected target volume or point, such as 634, has been done with respect to the external apparatus, such as the over-arm or the couch, then the aiming and referencing of a probe means or radiation beam relative to this apparatus can be done.

The graphic reference means could be attached to the patient's body as an alternative. By having markers on the body, such structures could be secured to the body for scanning and the data with fiducial markers used to put the anatomical data points in stereotactic coordinate space. Attachment to the body could be done with conformal means, straps, or stick-down devices.

Figure 7:
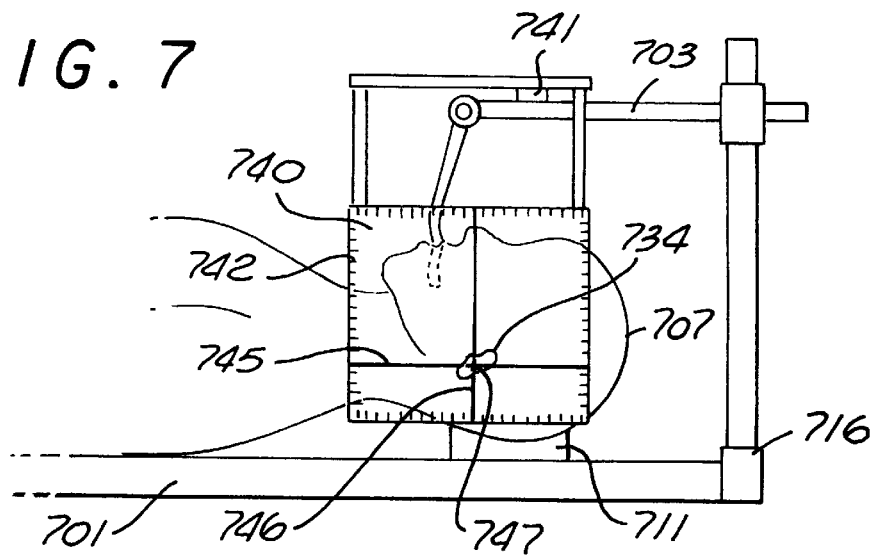
FIG. 7 shows a grid plate type target localizer system used with the over-arm.
Figure 8A:
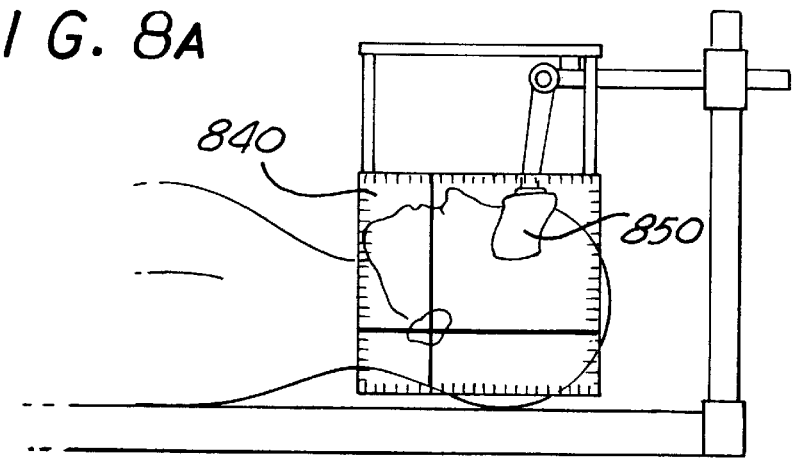
FIG. 8 shows other embodiments of the present invention without occipital molds and with external contour-based fixation.

FIGS. 6 and 7 illustrate how the referencing of external apparatus such as a radiation beam or stereotactic instrument can be done once the mapping of the scan image data to the external apparatus, such as the over-arm or couch, has been carried out. The patient would be lying on couch 701. This couch could be on a radiation treatment machine, and therefore not the same couch as that for the image machine shown in 601. Nonetheless, the arm can be secured to the couch by clamp 716 in a substantially identical way as was done in FIG. 6, and thus the orientation of the patient's anatomy 707 relative to the radiation or treatment couch can be placed identically. The over-arm assembly can be transferred, therefore, without changes in the articulation of the over-arm, from one couch to another to preserve the relationship between the patient's anatomy and the over-arm and/or the couch. In the case of FIG. 7, a target localizer which consists of a grid device 740 is attached to the horizontal arm element 703 by a clamp or securing element 741. The grid 740 has scales such as the markings 742 in the horizontal and vertical axes. By knowing the relationship of the patient's anatomy and the scan data to the over-arm, and by knowing the relationship of both the localizer elements in FIG. 6 as well as the target localizer 740 in FIG. 7 relative to the over-arm, then the relationship of the graphic reference means, the data mapping, and the target localizer can all be registered to the same stereotactic coordinate space, which could be the image scan data set from the scanner itself. Thus, the scales on the indicator 740 can be quantitative coordinates that are representative of the coordinates from the mapping from scanner data to the patient's anatomy, and thus to the external apparatus structure of the couch and the over-arm. In this way, a selected target volume from the image scan data such as 634 in FIG. 6, which corresponds to 734 in FIG. 7, can have specified AP, Lateral, and Vertical coordinates for x, y, z coordinates relative to the over-arm apparatus. These coordinates could be set by the horizontal line 745 and vertical line 746 as shown in FIG. 7, so the intersection point 747 could represent, for example, the centroid of the target volume 734 where the radiation beam can converge, i.e. the isocenter of a linear accelerator beams could converge. The target localizer plate with this planned target position 747 can then be used to orient the patient such that a selected physical point in the patient's anatomy can be placed at the radiation isocenter of the LINAC. This may be done by shining, for example, a laser beam on the cross 747 when the patient is lying on a LINAC couch 701 which would mean that the physical target in the patient's head associated with spot 747 lies on a line through the isocenter of the LINAC. By doing this in two dimensions, the physical coordinates in three dimensions of the selected target point can be set to the LINAC isocenter in space, and convergent beam therapy can begin. FIG. 8 illustrates variations of the embodiments of the previous figures. In this situation, the over-arm structures are relatively the same, and the target localizer 840 is shown with its target coordination lines. The patient attachment element 850 is shown here as a contoured element which may contour to the forehead, nasion, or other aspects of the patient's cranial external anatomy so as to stabilize the patient in position during scanning and treatment and to immobilize him during these episodes. Unlike FIG. 7, where there is a molded cushion 711, the patient in FIG. 8 simply lies flat on the couch table. This can be satisfactory in some situations.

Figure 8B:
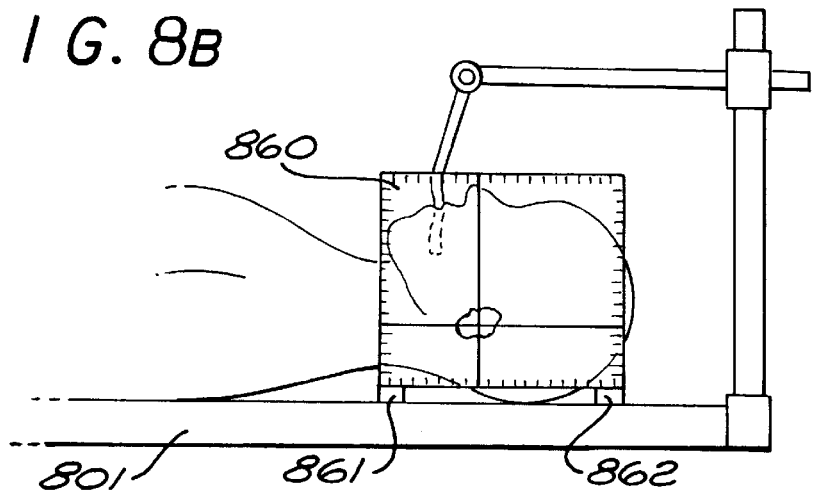

In FIG. 8B, an analogous embodiment is shown. In this situation, the target localizer 860, which again is a grid plates with scales on it, is attached directly to the couch 801 by securing means 861 and 862, rather than being secured to the over-arm itself. This is satisfactory if there is a very secure relationship between the over-arm assembly and the couch so the differential movement will not be a problem for accuracy and relocation.

Figure 9:
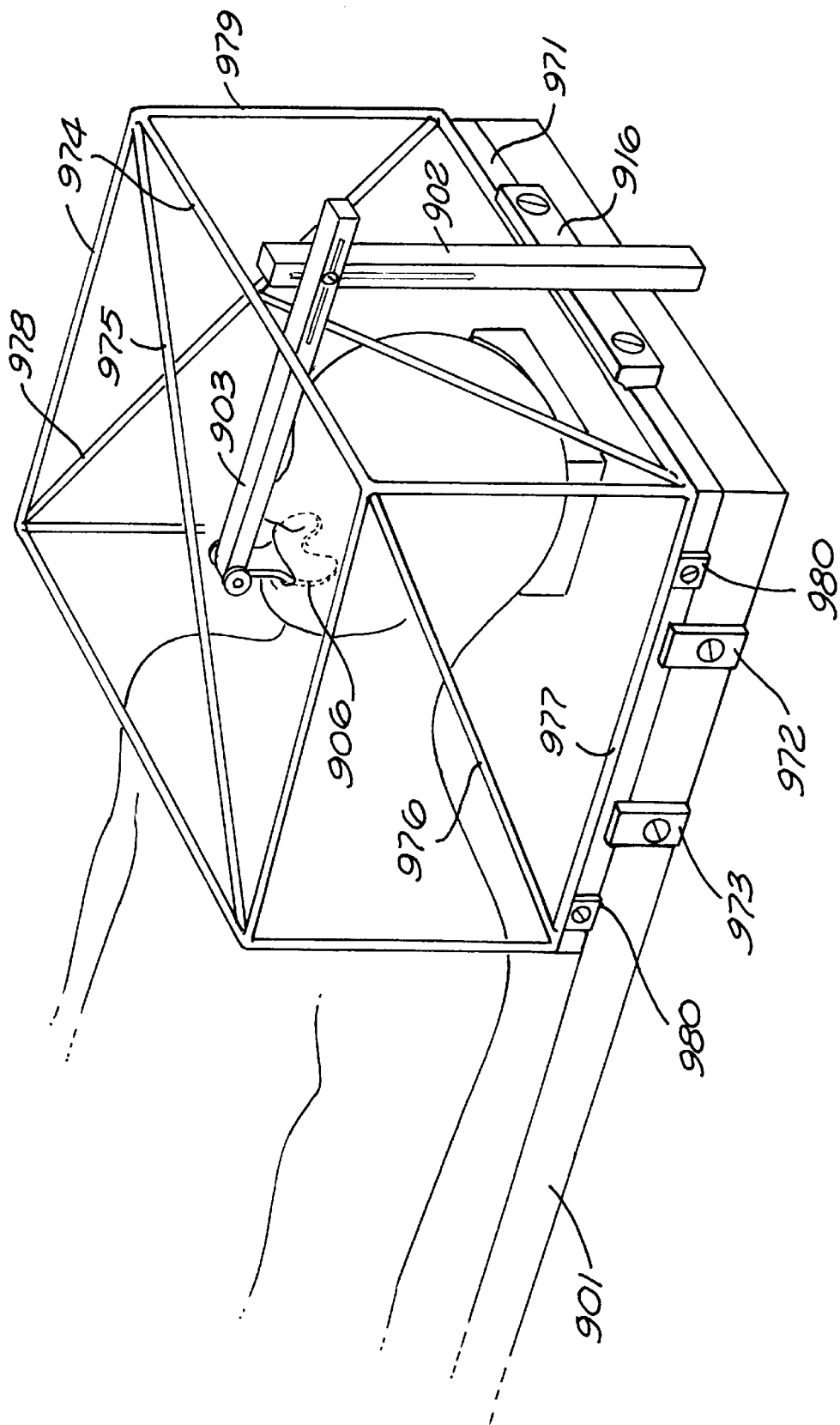
FIG. 9 shows a detail of the patient with the over-arm on a couch and a graphic reference means attached.

FIG. 9 shows yet another embodiment, in isometric view, which illustrates further aspects of the present invention. The over-arm is clamped onto a couch 901 by means of clamping plate 916, which in this case is clamped to a sub-plate 971 that in turn is secured to the couch by securing clamps 972 and 973. The over-arm has vertical elements 902, horizontal elements 903, and the dental tray is in place for 906. Securing straps, in this situation, are not shown, and although they are very important in some situations, they may not be necessary in other situations. If there is a cooperative patient, for example, the patient can essentially bite on the dental tray during the duration of the scanning and the treatment, and this positions him relatively well. The graphic reference means has a series of horizontal rods, for example, element 974, and diagonal rods, such as 975, not only on the top but also on the sides, illustrated by the diagonal rods 976 and the horizontal rods 977. On the opposite side there are further diagonals 978, and on the corners there are rods illustrated by 979. You can see by these rods that slice image data from slices, either axially, sagittally, or coronally through the patient's anatomy, can give rise to index data in the image slice data that can map the anatomy and pathology of the patient to the coordinate frame of the over-arm or the couch. In this situation, the graphic reference means happens to be secured to the sub-plate 971 by clamps illustrated by 980.

Figure 10:
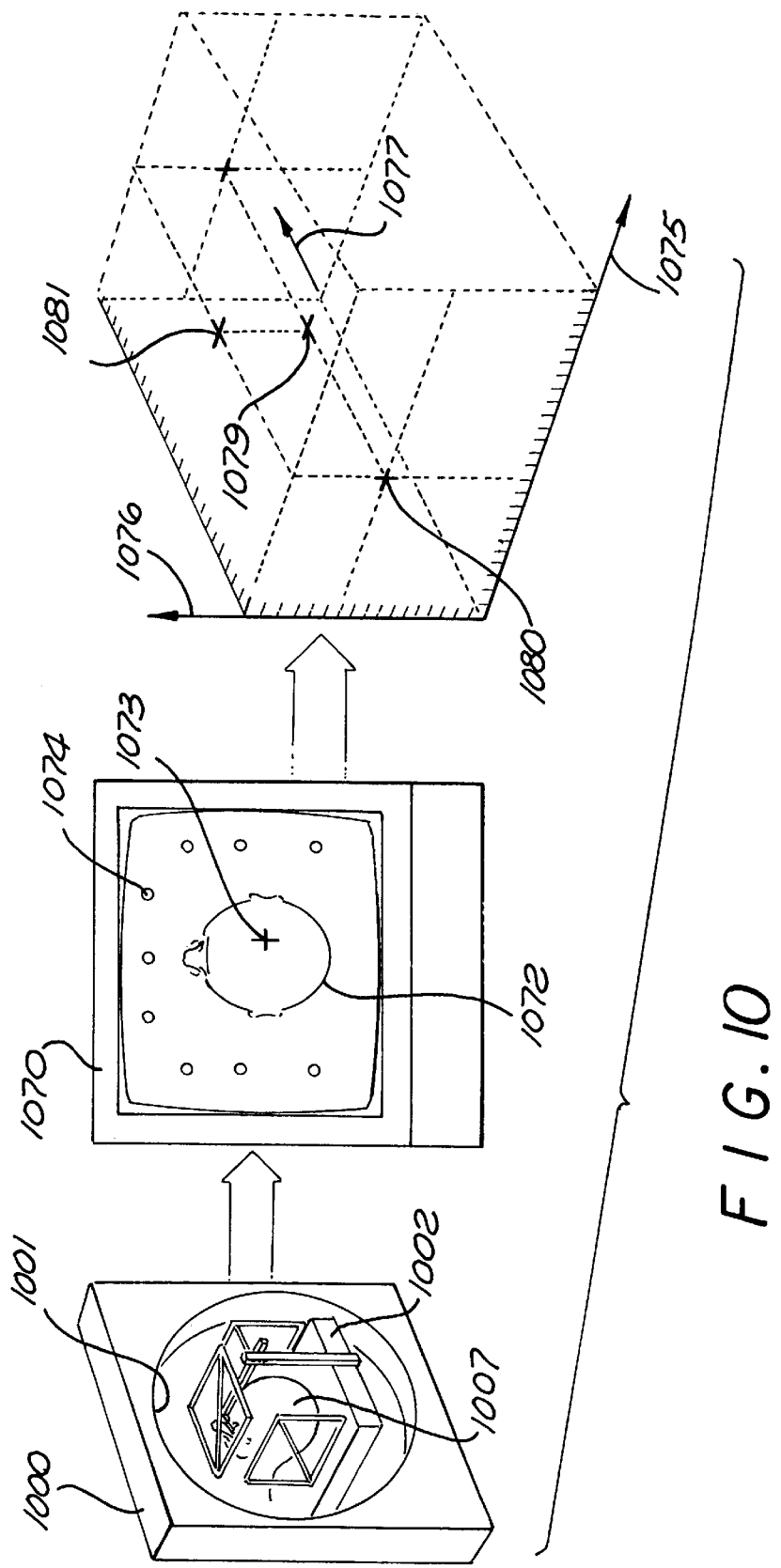
FIG. 10 shows the mapping of tomographic data to a coordinate frame referenced to the over-arm and the couch.

The scheme of transforming from scan image data to the coordinate reference frame of the couch, which might be a linear accelerator couch, is illustrated by the embodiment shown in FIG. 10. An image scanner 1000 has characteristic scanner aperture 1001, and the patient 1007 is on the scanner couch, represented by 1001 in the aperture of the scanner. Localizers with vertical and diagonal elements and the over-arm assembly are illustrated but not numbered in the left-hand figure of FIG. 10. The intersection of the patient's anatomy and the graphic reference means gives rise, in the CT case, to image scan data represented in two dimensions and shown in the middle figure of FIG. 10. In that middle figure is shown a computer console 1070, which is part of a computer graphic workstation. This could be a part of the image scanner itself, which takes the raw image scan data from the scanner 1000 and processes the data to provide two-dimensional graphics display for each slice, in the case of tomographic CT scanners. The patient's anatomy is shown by the figure 1072 and a selected target point by the cross 1073. The index marks, such as 1074, represent the intersections of the image scan slice plane with the rods and diagonals of the graphic reference means around the perimeter of the patient's head. These provide the information to transfer from the two-dimensional coordinate space of the image slice to the three-dimensional coordinate space of the over-arm or equivalently the couch and localizer, since there is a known relationship between the localizer and the over-arm and the couch. The means of transforming from the two-dimensional coordinate system of the image scan data to the three-dimensional coordinate system is well known in the art, and can be done graphically or non-mathematically by measuring distances on the scanner image or by doing mathematical transformations and other processes. Once all of the two dimensional scan image data is transferred to the stereotactic coordinate system of the over-arm and the localizer, then the entire data stack can be put into a three-dimensional representation if desired, and targets and anatomical structures outlined, contoured, and segmented. Calculations of trajectories of beams can be done, and paths for stereotactic probes or radiation beams through the tissue in three dimensions to achieve a given target position or target volume can easily be done. This is advantageous for three-dimensional treatment planning. An example of an existent 3-D planning system is the XKnife stereotactic radiosurgery and stereotactic radiotherapy programs from Radionics, Burlington, Mass. Once the selected target point 1073 has been made, its coordinates relative to the space of the over-arm and/or the space of the graphic reference means and couch can be determined. Referring then to the right-hand figure in FIG. 10, the coordinate axes are indicated by the axis lines with arrows 1075, 1076, and 1077, which could be, respectively, the Vertical, AP, and Lateral axes relative to the patient or the couch. The target position in this coordinate space is represented by the point 1079, and this would correspond to the selected target point, for example 1073, in one of the scan image data two-dimensional data sets. The coordinate reference frame represented by the axes 1075, 1076, and 1077 also have scale lines on them indicated by the tick marks on those axes, and these would correspond to a quantitative coordinate measuring scale associated with the graphic reference means and also specifically referenced to the over-arm structure and/or the platform 971, to which it is attached in the example of FIG. 9. The coordinate position in this coordinate reference frame of the selected target position is indicated by 1079, and the projection of that coordinate position onto, for example, the projected, two-dimensional axis plane of 1075 and 1076 may be represented by the point 1080. Similarly, the projection onto the axis plane associated with 1075 and 1077 would be indicated by the point 1081. These, then, would be the projected target points which are sought to be aligned with laser lights that are coincident with the principle axes of a linear accelerator, for example, passing through the isocenter of the linear accelerator. In this situation, such an alignment would mean that the isocenter of the linear accelerator would be coincident in space with the point 1079.

Figure 11:
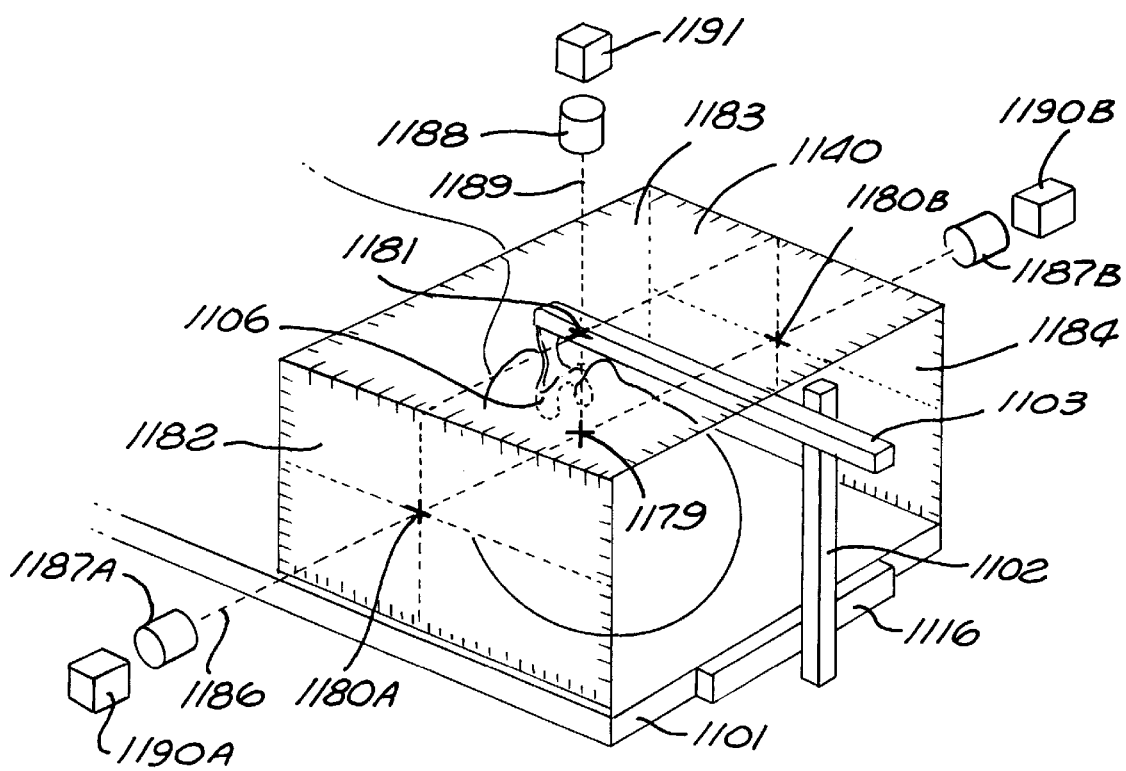
FIG. 11 shows the use of the grid type target localizer together with co-aligned laser and X-ray machines for target positioning and incremental target shifting using projective X-ray images on the principal couch axes true isocenter.

The alignment of the target coordinate space to the physical space of a stereotactic treatment machine, such as a radiation machine like a LINAC, is shown in FIG. 11. Here the over-arm vertical elements 1102 may be attached via the bracket 1116 to the LINAC couch 1101. The over-arm horizontal element 1103, again, holds the dental piece 1106 in exactly the same orientation as in FIG. 9, recalling that in FIG. 9 the patient was arranged in the same orientation on the scanner couch for a tomographic scan. In FIG. 11, a target localizer box 1140 is used to provide the coordinate scale references so that a physical point associated with the projected target point, as in 1080 and 1081 in FIG. 10, can be achieved. The localizer box has a side plate 1182, which will correspond to the coordinate projected plane 1075 and 1076 in FIG. 10. Similarly, the upper physical plate 1183 would correspond to the two-dimensional coordinate plane 1075 and 1077 in FIG. 9. In addition, a plate on the opposite side, indicated by 1184, which is the analog to plate 1182, again corresponding to the projected plane perpendicular to the 1077 axis in the stereotactic coordinate system. The projected point of the selected target point can be then graphically marked or located on these side plates and would correspond to the projected point 1180A on the plate 1182, this corresponding to the projected point 1080 in FIG. 9. The equivalent point 1180B represents the projection of a line parallel to the 1077 axis through the selected target point 1073 and 1079 in FIG. 10. The physical point in space 1179 lies on the line between 1180A and 1180B. That line through the selected target point is represented by 1186 in FIG. 11. There are lasers 1187A and 1187B which are lined up in the linear accelerator (LINAC) target room and passed through the isocenter point 1179, if properly aligned. Similarly, a laser 1188 sends a laser beam along the line 1189, which passes through the isocenter 1179 and is typically in a vertical aspect in the LINAC target room. Thus, if the patient couch is moved such that the projected target points 1180A and 1180B coincide with the laser spots which are shining along the line 1186 and this laser line passes through isocenter, then the selected target point will also lie coincident along this line. Looking at the corresponding plate 1140 which is perpendicular to the vertical axis 1189, the projected target point is indicated here as 1181, and can be marked on that plate. Aligning the vertical laser beam along axis 1189 to coincide with the target projection point 1181 on the plate 1140 will assure that the selected target point lies on the LINAC isocenter axis, which is vertical and coincident with the laser line 1189. If the horizontal and vertical laser lines are so aligned with the target localizing plate, then the selected target point 1179 will lie at the isocenter of the linear accelerator, and to that isocenter point all radiation beams from the linear accelerator will converge. This is an example of aligning a target determined from graphic imaging using the patient immobilizer device of the present invention and the graphic reference means and to set that selected target point physically in space at the convergence point of a isocentric linear accelerator. A similar process could be conceived for a stereotactic frame or a robotic system which is to achieve a target determined from tomographic scanning in the head and neck region.

Another feature shown in FIG. 11 are X-ray machines indicated by 1190A and 1190B that are, for the particular example of FIG. 11, aligned along the axis 1186, and thus coincident with the laser beams and pass with their central beam through LINAC isocenter at 1179. These X-ray machines can be used to produce real-time fluoroscopic X-ray views of the patient's anatomy and of radiopaque index markers on the target localizer for further real-time update of the patient positioning and the selected target position relative to isocenter. A similar laser 1191 is aligned with the vertical axis 1189 for a similar purpose. Comparing the images through the actual patient's anatomy from such co-linear X-ray machines with the reconstructed projected images based on the three-dimensional data of the patient's head can confirm the alignment of the patient with the isocenter and also confirm the orientation of the patient's head on the couch. This can be very important in the skull base, head and neck, and cervical and high thoracic areas where articulation of the bony structures in the spine could be present and misalignments could occur due to flexing of the body. Small movements in the x, y, z (or AP, Lateral, and Vertical) directions of the LINAC couch could correct for such deviations. That is to say, a visual or quantitative comparison between the actual projected X-ray image and the reconstructed projected X-ray image on the computer workstation (that comparison could, for example, be made on the computer workstation display 1071) could be used to determine corrective, discrete, incremental movements of the couch 1101 along the axes corresponding to 1075, 1076, and 1077 of FIG. 10 so as to bring into coincidence or to align said two images and this to correct for target misalignments directly, based on the patient's anatomical X-ray images. This trimming process, if done for example in Cartesian coordinates, would be very simple and easily understood by a radiotherapist technician, and could lead to a much more highly precise alignment, especially in critical areas near the spine. It could also lead to minor angulation orientations of the patient's head as, for example, around the joint 405 in FIG. 4 so as to best align the spine and the selected target point relative to isocenter.

Thus, as part of this invention, in addition to the patient immobilization devices used in conjugation with the graphic reference means and/or the target localizer means, I claim the use of X-ray machines, which may or may not be aligned or substantially aligned along the coordinate axes of the stereotactic structure which is being used to determine stereotactic coordinates from the graphic reference means. In the case of radiation delivery systems, the coordinate axes for a LINAC, for instance, may be the Cartesian coordinate axes that pass through the isocenter of the LINAC, if the LINAC is of an isocentric type, and that is the usual type today. These axes are typically the gantry axis of the LINAC, which is a horizontal axis; the vertical axis, which passes through the isocenter and intersects the gantry axis; and a second horizontal axis, which passes through isocenter and is perpendicular to the gantry axis. It is typical in such LINAC set-ups to have laser lights that are aligned through isocenter and parallel to the vertical axis and to the horizontal axis that is perpendicular to the gantry axis. The X-ray machines shown in FIG. 11 could be co-linear with those Cartesian laser set-ups, and thus co-linear with the LINAC isocenter axes, as described above. Use of standard X-ray imaging planes associated with these X-rays or real-time fluoroscopic X-ray images that can be downloaded directly to the computer workstation, as in FIG. 10, with means for comparing the X-ray images from projected X-ray images from such X-ray machines with the reconstructed projected X-ray images from the three-dimensional data set from the imaging machine can be done in the computer workstation, as in FIG. 10. Means for reading out simply the translation of the couch so as to best merge such projected X-ray images and reconstructed projected X-ray images could be done in software in the computer workstation. Image fusion algorithms that automatically do such merging and optimization of projected images could be invoked. The mounting device, viz. part of 1116 for example, which holds the over-arm apparatus, may include the simple means of knobs which can be turned by hand so as to best trim in or make overlap bony structures seen in both of these images. The real X-ray images and the synthesized X-ray images could easily be implemented on such a workstation. This would give read-out data for couch x, y, z movement when the couch is in the so-called zero-degree position, that is, pointing straight out from the gantry axis so that the patient's anatomy could be best trimmed in prior to irradiation. Simple Cartesian movements of the couch are far easier than attempting to invoke all the rotational axes that are possible, although complex rotation and translation movements of the couch are easily calculated to make target position corrections far more complex situations. Typically, the patient is aligned on the couch as one looks from the ceiling relatively well. The arch of the spine as one looks at an elevation view, as in FIG. 5, is a consideration, and here, looking at the vertebrae in such synthesized and real projective views, could help trim in a selected target position when it is critically close to the spinal column and thus very high precision, and incrementation of the patients position would be needed. In this context, too, the present invention is useful because the over-arm means of patient immobilization is relatively unobstructive to such X-ray shots. A choice of low-density materials for the over-arm and for the dental or surface contour of patient contacting means would be an advantage here for an X-ray shot taken along the vertical axis. The X-ray machines need not be permanently mounted colinear with the laser lights or with the LINAC axes. The X-ray machines could be of the portable variety, such as common fluoroscopic machines, and moved into place next to the LINAC at the time that the projected X-ray view is needed to confirm patient position. The X-ray machines could also be mounted on or in the LINAC gantry itself, and the gantry may be swung into position with the LINAC axes to either vertical or horizontal, and thus in this position such X-ray shots could be taken of the mounted X-ray machines to produce such projected images.

It should be noted that the graphic reference means could also be cooperatively coupled to the patient himself, as with a skin-type localizer or something directly coupled to a dental tray. In such a way, a reference can be made between the patient's anatomy and the over-arm structure or a target localizer in a way analogous to that described above in the embodiments where the graphic reference means was directly attached to the over-arm. The localizer markers could be discrete X-ray opaque structures, dots, or rings stuck to the patient's skin at, for example, positions marked by ink tattoos. The localizer could involve one, two, three, or more N-shaped, V-shaped, or other varying shaped structures to give varying or otherwise recognizable fiducial marks on the image scan data to develop a mapping or correspondence between the patient's anatomy and targets to the over-arm, patient attachment means, or couch structures. These contexts are all also claimed within the scope of the present invention.

Figure 12:
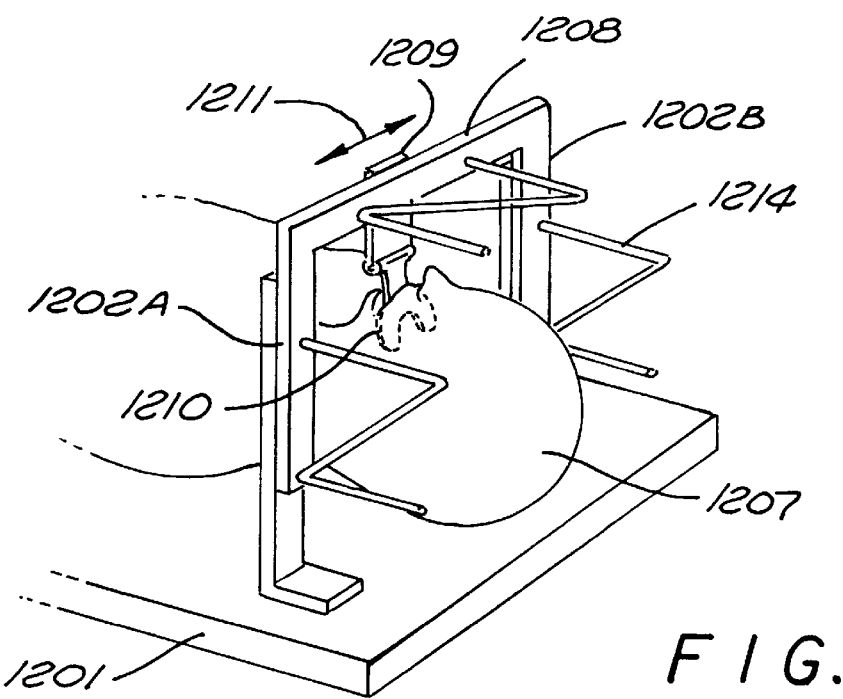
FIG. 12 shows an over-arm structure with two side brackets and attached graphic reference means.

FIG. 12 shows another embodiment of the present invention in which the apparatus includes upright elements 1202A and 1202B which are on opposite sides of the patients anatomy 1207, and there is a cross-member 1208 with patient attachment bar 1209 that couples to a dentition form or bite piece 1210. The attachment element 1209 may slide back and forth as indicated by the arrow 1211. The uprights 1202A and 1202B may also be adjusted vertically to accommodate the patient's head. These uprights attach in a fixed or possibly variable position relative to the couch 1201. The graphic reference means are illustrated by the N-shaped structures 1214, which are on both sides and the front in this example. Only one of these N-shaped structures need be used if the patient is aligned to the CT or MRI scanner beforehand. The N-shaped structures may be replaced with simple V-shaped structures or a single rod and a diagonal or any other graphic reference means which provides variable data within the various image slice data so as to determine where a selected target within the patient's body is in the coordinate space of the couch or the uprights or over-arm.

Figure 13:
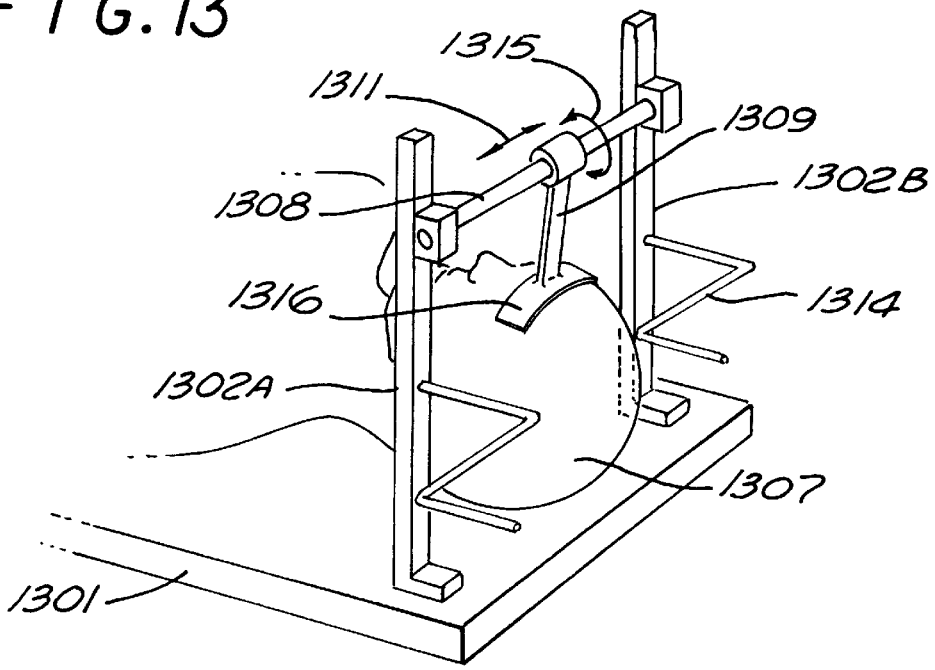
FIG. 13 shows a double upright structure with adjustable patient holding device using an external contour patient attachment.

FIG. 13 shows another example of a bilateral patient immobilization device with upright structures 1302A and 1302B and cross-member 1308 with patient attachment element 1309 which may have a lateral variation, as shown by the arrow 1311, as well as a rotation degree of freedom as indicated by another arrow 1315. In this case, there is a cast or form element 1316 which contours to the patient's anatomy or head 1307. This cast or form could be a mask of thermoplastic material that can be shaped to the patient's head, neck, or torso. Again, graphic reference means are shown in this case, illustrated by 1314 as an N-shaped structure on one side of the patient's head, and another on the other side of the patient's head.

Figure 14:
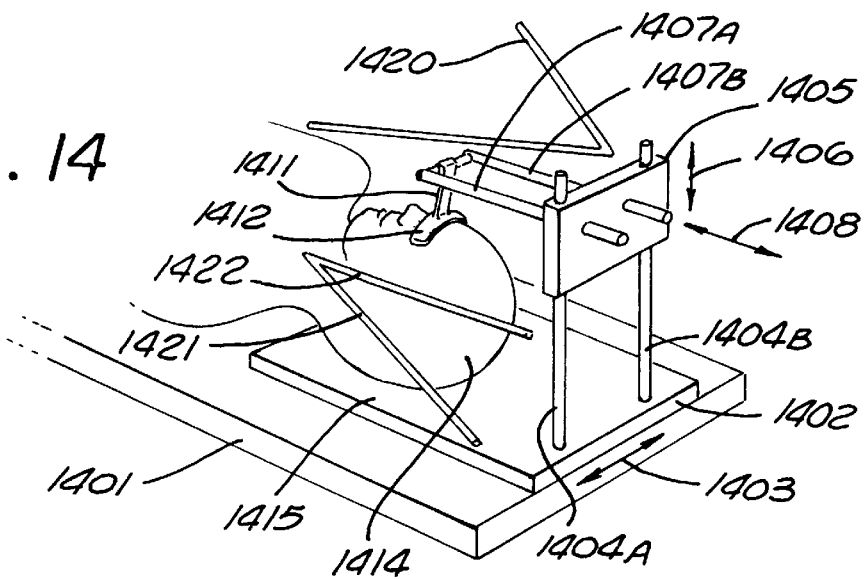
FIG. 14 shows a dual over-arm structure with external contour attachment together with a base plate and diagonal graphic reference means.

FIG. 14 illustrates yet another variation of the head and neck immobilization and referencing structure. In this case, attached to couch 1401 is a base element 1402 which may slide back and forth according to the arrow 1403, and there are uprights 1404A and 1404B, onto which is a slider 1405 so that the slider can move up and down according to the arrow 1406. Furthermore, there are horizontal bars 1407A and 1407B which enable sliding in the direction illustrated by the arrow 1408 so that the patient applicator or patient attachment means, illustrated by the element 1411, can be adjusted so as to accommodate the patient's head. In this case, a form device 1412 is used to capture the shape of the patient's face in his nasion or forehead region. This patient attachment element 1411 and patient contour element 1412 can be angulated, fixed, and held in position according to the desired angulation of the patient's head 1414. A base plate 1415 holds the entire assembly and may be put back repeatedly in the same position on the couch according to the fractionation of treatments. The graphic reference means in this case is illustrated by a top element 1420, which is in the shape of a V, that is, two rods or other elements which form a triangular shape such that CT tomographic slices or reconstructive slices through the anatomy and the graphic reference means give varying displacement of index dots according to the slice position. On one side of the patient is another graphic reference device which includes a diagonal 1421 and a rod 1420 to form a triangle with the same function as the triangle on top, but giving further information about the orientation and position of any image slice through the patient's anatomy and through the localizer. A similar device could be placed on the opposite side of the patient's head or underneath the patient's head within the base element 1415 for further information. These are illustrations of the kinds of variation of graphic reference means which might be used involving plates, rods, diagonals, or other type elements. FIG. 14 illustrates the use of an over-arm structure which has multiple struts and rods to give stability and yet achieve better sliding. These struts and arms give variability of positioning relative to the patient's head during the setup to achieve the best orientation of the head for the stereotactic treatment and imaging.

Figure 15:
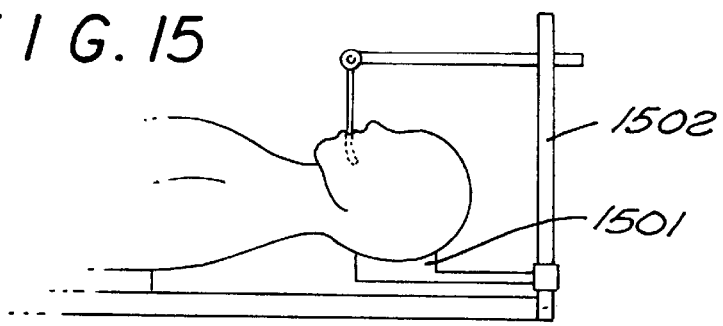
FIG. 15 shows an embodiment wherein the occipital support or mold is attached to the arm and may or may not have an adjustment in position relative to the over-arm or upright structure.

There are many variations of the present invention which are possible to implement by those skilled in the art, and such variations are intended to be within the scope of the present invention. The above embodiments are only meant as illustrations of the concept of the invention. For example, a wide range of construction and configuration of the head and neck over-arm structure could be imagined. The vertical and horizontal members, for instance, as shown in FIGS. 2, 3, 4, and 5, rather than being single members could be bi-lateral structures or tubes or rods, and a sliding joint could accommodate such bi-lateral structures for easy sliding and clamping. The over-arm bar 203, for example, in FIG. 2, rather than being a square bar could be a round tube, or it could be two tubes or two bars spaced several centimeters apart so that it passes over the anterior portion of the patient's head clearing the nose and having a gap at the midline. Similarly, the vertical structure 202 could be bilateral rods, and the junction between 203 and 202 could be a right-angle bracket which has two holes for sliding purposes. The use of biasing straps, rods, strings, pulls, etc. as in FIG. 3 or no biasing straps in FIG. 2 is possible. Other forms of biasing could be devised in the form of mechanical structures that go up and over the patient's head for better stabilization of a dental tray or a pad over the patient's forehead or nose region, or so that counter forces can be applied to the patient's cranium at top or back. Side clamps on the temples could be used to prevent patient head rotation. Beanbags, foam pads, molded plastic cushions, or molded silicone cushions are examples of structures that could be used to fixate the patient on his external anatomy or his occipital protuberance, and these could be used with the over-arm as patient attachment means, or as added patient immobilizers. FIG. 15 shows the occipital cushion 1501 attached directly to or part of the over-arm or upright structure 1502, rather than being on the couch. The over-arm itself could take on a variety of shapes and structures. Rather than being a series of semi-orthogonal rods which slide, it could be articulated links with rotation joints between that can be clamped sequentially. Other rotation angles could be present, rather than the one at point 205 in FIG. 2. Rotations at each of the joints could make a more fluid, three-dimensional articulation of the arm in space, and thus the arm could be positioned by the operator in a convenient orientation relative to the patient's head, depending on the chosen radiation or treatment that will be delivered subsequently. Such articulations could be digitized and quantitated to frameless stereotactic or even real-time positioning with digital readout of the patient's position. If, for example, the left side of the head is to be favored in terms of treating, the arm could be brought up from the right side of the patient's head somewhat as shown in FIG. 3. It could arc over the head in a curvilinear arc rather than rectangular arms as shown in the above embodiments. The arm could have rotating links which are locked securely at the linked joints. The joints could be mechanically digital in nature as in starbursts for the Mayfield Headrest, preventing any possibility of movement. The scales could be put on each of the arm links so that they could be reset quantitatively, and thus do not have to be stored with one patient for the duration of his fractionated radiation treatment, but could be used for many patients during the course of their treatments simply by setting numbers on the scales to repeat the orientation, position, and configuration of the arm immobilizer.

The graphic reference means could take many forms, shapes, and configurations, as partially discussed above. They could be CT and MRI compatible devices that could be used for both modalities. P.E.T. scanning or plane X-ray detectable structures could be used for invoking these imaging modalities as well as part of the coordination towards a selected target point or proper registration of the anatomy prior to and during treatment as associated with the treatment plan and implementation of the actual dosimetry. For example, the graphic reference means, as shown in FIG. 9, could have radiopaque reticules and grids on it or index points such that angiographic shots or plane X-ray or fluoroscopic views could be taken as well to coordinate the position of the anatomy relative to the arm structure or other reference external apparatus. The graphic reference means could have discrete or linear objects which can be seen in one or more slices so as to reference it. It could have indent points or divots so that the frame could be coordinated by means of a digital navigator with respect to external contours of the patient's head so as to reference the patient's anatomy to the over-arm, the couch, the head cushion, base plates, or target localizer. Such transfer by means of frameless navigation would eliminate the need for the localizer to be used during the image data collection phase, but rather an image data set could be taken without a localizer, and the registration of the patient to the external apparatus such as the over-arm or other docking structures could be done by transfer means using an electronic digitizer as a frameless operating arm, LED tracking system, magnetic tracking system, or simply mechanical transfer of a pointer with scales in the coordinate reference frame of the arm or subsequently of the target localizer structure. These are all alternative methods of a graphic reference means or graphic reference device for mapping or transferring the image data of the patient's head to a coordinate reference frame or structure associated with the patient immobilizer and target localizer.

Many forms of target localizer could also be invoked. Rather than grid plates, as shown in FIG. 11, the target localizer could be sliders with bomb sites or cross-hairs; it could be digitized readouts of cross-hairs that could be coincident with the laser lights for alignment. The target localizer could be attached to the couch, the over-arm, the patient, or the patient contact means. The target localizer and the graphic reference means could be integrated or combined in one structure, rather than separate structure. All of these types of target localizers are claimed under the scope of the present invention.

The use of the present stereotactic methodology for skull-based head and neck and high thoracic targets can have powerful impact on the precision, reliability, reproducibility, and real-time dynamic tractability of a patient and internal anatomy in the treatment of cancerous tumors of the head and neck. A stereotactic apparatus could be invoked in addition to or in conjugation with a target localizer to pass a probe to a target or to guide otherwise treatment modality to a target, as described in the present invention. Having the open approach of beams, spanning a very large solid angle, as illustrated by the use of the over-arm, has the great advantage of reducing untoward radiation effects on the patient such as skin dose from electrons and brings further advantages over the previous ring-based stereotactic immobilization devices.

Having so described embodiments of the present invention, what I claim here is the following:

1. A stereotactic head and neck localizer adapted to immobilize the head and neck region and the head of a patient on a couch for the purpose of acquiring scanner image data from an image scanner and/or locating said head of patient in a stereotactic spatial relationship to a stereotactic treatment machine comprising:

a. a head immobilizer which includes at least one sagittal plane over-arm structure which is generally an elongated structure which is attached on one end to said couch and having on the opposite end of said over-arm structure a head attachment element which conforms to a portion of said head of the patient so as to orient said head of patient with respect to said over-arm structure;

b. a graphic reference adapted to be placed in a known position with respect to said over-arm structure, and including reference indicia such that when said head of patient is scanned in said image scanner, said reference indicia are detectable as part of image scan data from said image scanner, said image scan data thereby being used to determine a target coordinate(s) of a selected anatomical target in said scanner image data with respect to a reference frame of said over-arm structure.

2. The apparatus of claim 1 wherein said sagittal plane over-arm structure includes a first end that is securely attached to said couch, and an adjustable, elongated arm element which connects said first end to a second end of said over-arm structure, said second end comprising said head attachment element, and said adjustable, elongated arm element having adjustment means so that the position of said second end can be adjusted with respect to said first end, such that when said first end is securely attached to said couch, said second end, and therefore said head attachment element, can be moved to said portion of said head of patient to conform to said portion of said head of patient, and therefore immobilize said head of patient with respect to said couch.

3. The apparatus of claim 1 wherein said head attachment element comprises a dental piece that fits to the teeth of said head of patient.

4. The apparatus of claim 3 and further including a biasing means which pushes said dental piece with an adjustable force against the upper teeth of said head of patient.

5. The apparatus of claim 4 wherein said biasing means comprises a strap which couples to said dental piece and is adapted to extend on the top of said head of patient without transmitting substantial forces through said sagittal plane over-arm structure.

6. The apparatus of claim 1 wherein said head attachment element comprises a mold of a portion of said patient's face, said mold being repeatedly fittable to said portion of said patient's face.

7. The apparatus of claim 1 and further including an occipital conforming element which substantially conforms to the shape of the occiput of said head of patient and which is adapted to be cooperatively coupled to said over-arm structure and/or said couch so as to further stabilize said head of patient when said head immobilizer is attached to said head of patient and said couch.

8. The apparatus of claim 1 wherein said graphic reference includes at least one diagonal element which is part of said reference indicia and which produces variable data in said scan image data which can be used to determine said target coordinate of said selected anatomical target with respect to said head attachment element.

9. The apparatus of claim 8 wherein said sagittal plane arm-like structure is adapted such that it can be oriented in a substantially sagittal plane with respect to said head of patient.

10. The apparatus of claim 1 wherein said sagittal plane over-arm structure is adapted to be attached repeatedly to said couch in substantially the same orientation with respect to said couch, and thereby said head of patient, when immobilized by said head immobilizer, can be oriented repeatedly in substantially the same orientation with respect to said couch.

11. The apparatus of claim 1 wherein said sagittal plane over-arm structure is an arm-like structure which is adapted to extend from its said one end to said couch over said head of patient such that said head attachment element on said opposite end can be positioned substantially over said head of patient when said head of patient is on said couch.

12. The stereotactic head and neck localizer of claim 1 wherein said graphic reference is attached to said at least one sagittal plane over-arm structure.

13. An apparatus adapted to immobilize a portion of a patient's body on a couch and/or for acquiring scan image data from an imaging scanner comprising:
   a. at least one upright structure which has a first end which can be secured to said couch, and a second end which includes a patient attachment element which conforms to said portion of said patient's body so as to immobilize said portion of said patient's body with respect to said upright structure and said couch;
   b. graphic reference means which is adapted to be cooperatively connected to said upright structure and including reference indicia, said graphic reference means being adapted so that when said graphic reference means is scanned in said image scanner with said portion of said patient's body being immobilized by said patient attachment element, said reference indicia are detectable as reference index data as part of said scan image data from said image scanner such that said scan image data can be used to determine a target position of a selected anatomical target in said portion of said patient's body with respect to said patient attachment element.

14. A stereotactic head and neck localizer adapted to immobilize the head and neck region and the head of a patient on a couch for the purpose of acquiring scanner image data from an image scanner and/or locating said head of patient in a stereotactic spatial relationship to a stereotactic treatment machine comprising:
   a. a head immobilizer which includes at least one sagittal plane over-arm structure which is generally an elongated structure which is attached on one end to said couch and having on the opposite end of said over-arm structure a head attachment element which conforms to a portion of said head of the patient so as to orient said head of patient with respect to said over-arm structure;
   b. a target localizer that is adapted to be fixed with respect to said over-arm structure in a known position and including target coordinate indicator so that said target coordinates of said selected anatomical target can be set on said target coordinate indicator, and said target coordinate indicator can be used to physically reference the position of said selected anatomical target with respect to an external treatment apparatus.

15. The apparatus of claim 14 and further including at least one X-ray machine which can be aligned with respect to the reference frame of said target localizer so that projected X-ray images of said head of patient using said at least one X-ray machine can be used to confirm the proper relationship of the anatomy of said head of patient with respect to said target localizer.

16. The stereotactic head and neck localizer of claim 14 wherein said target localizer is attached to said at least one sagittal plane over-arm structure.

17. A stereotactic head and neck localizer adapted to immobilize the head and neck region and the head of a patient on a couch for the purpose of acquiring scanner image data from an image scanner and/or locating said head of patient in a stereotactic spatial relationship to a stereotactic treatment machine comprising:
   a. a head immobilizer which includes at least one sagittal plane over-arm structure which is generally an elongated structure which is attached on one end to said couch and having on the opposite end of said over-arm structure a head attachment element which conforms to a portion of said head of the patient so as to orient said head of patient with respect to said over-arm structure;
   b. a graphic reference adapted to be placed in a known position with respect to said over-arm structure, and including reference indicia such that when said head of patient is scanned in said image scanner, said reference indicia are detectable as part of image scan data from said image scanner, said image scan data thereby being used to determine a target coordinate(s) of a selected anatomical target in said scanner image data with respect to a reference frame of said over-arm structure;
   c. a target localizer that is adapted to be fixed with respect to said over-arm structure in a known position and including target coordinate indicator so that said target coordinates of said selected anatomical target can be set on said target coordinate indicator, and said target coordinate indicator can be used to physically reference the position of said selected anatomical target with respect to an external treatment apparatus.

* * * * *